United States Patent
Wu et al.

(10) Patent No.: US 12,261,580 B2
(45) Date of Patent: Mar. 25, 2025

(54) DEVICE AND METHOD FOR DETECTION

(71) Applicant: HTC Corporation, Taoyuan (TW)

(72) Inventors: Chun-Yih Wu, Taoyuan (TW);
Ta-Chun Pu, Taoyuan (TW);
Yen-Liang Kuo, Taoyuan (TW);
Wei-Chih Chang, Taoyuan (TW)

(73) Assignee: HTC CORPORATION, Taoyuan (TW)

( * ) Notice: Subject to any disclaimer, the term of this patent is extended or adjusted under 35 U.S.C. 154(b) by 302 days.

(21) Appl. No.: 17/955,684

(22) Filed: Sep. 29, 2022

(65) Prior Publication Data
US 2024/0113676 A1 Apr. 4, 2024

(51) Int. Cl.
*H03H 3/02* (2006.01)
*A61B 3/125* (2006.01)
*H03H 9/17* (2006.01)

(52) U.S. Cl.
CPC ............... *H03H 3/02* (2013.01); *A61B 3/125* (2013.01); *H03H 9/17* (2013.01)

(58) Field of Classification Search
CPC . H03H 3/02; H03H 9/17; A61B 3/125; A61B 5/6803; A61B 5/002; A61B 8/10; A61B 5/0507; A61B 5/1072; A61B 5/1075; A61B 5/6821; A61B 5/163; A61B 5/165; A61B 3/112
USPC .......................... 333/133, 186–188, 193–196
See application file for complete search history.

(56) References Cited

U.S. PATENT DOCUMENTS

| | | | |
|---|---|---|---|
| 6,120,460 A * | 9/2000 | Abreu | A61B 5/14546 600/405 |
| 6,312,393 B1 * | 11/2001 | Abreu | A61B 5/1455 600/558 |
| 6,423,001 B1 * | 7/2002 | Abreu | A61B 3/1241 600/404 |
| 10,314,530 B2 * | 6/2019 | Pugh | A61B 5/18 |
| 10,419,860 B2 * | 9/2019 | Cahan | H04R 17/00 |
| 11,256,096 B2 * | 2/2022 | Samec | A61B 3/063 |
| 11,370,185 B2 * | 6/2022 | Van Heugten | B29D 11/00817 |
| 2003/0069489 A1 * | 4/2003 | Abreu | A61B 5/14539 600/405 |
| 2009/0027280 A1 * | 1/2009 | Frangioni | A61K 49/0032 343/873 |
| 2017/0042480 A1 * | 2/2017 | Gandhi | A61B 5/14546 |
| 2019/0090737 A1 * | 3/2019 | Pugh | A61B 5/14555 |
| 2022/0011603 A1 * | 1/2022 | Howell | G02C 5/001 |
| 2022/0133212 A1 * | 5/2022 | Krueger | A61B 3/0041 600/301 |

(Continued)

FOREIGN PATENT DOCUMENTS

WO    WO-2021172245 A1 *  9/2021

*Primary Examiner* — Rakesh B Patel
*Assistant Examiner* — Jorge L Salazar, Jr.
(74) *Attorney, Agent, or Firm* — Birch, Stewart, Kolasch & Birch, LLP

(57) ABSTRACT

A detection device for detecting an eyeball includes a frame element, a transceiver, and a contact lens element. The transceiver is disposed on the frame element. The transceiver transmits a first RF (Radio Frequency) signal. The contact lens element includes a resonator. The resonator converts the first RF signal into a first ultrasonic signal. The first ultrasonic signal is transmitted to the eyeball. The resonator converts a second ultrasonic signal from the eyeball into a second RF signal. The transceiver receives the second RF signal.

19 Claims, 5 Drawing Sheets

(56) References Cited

U.S. PATENT DOCUMENTS

2022/0219197 A1\* 7/2022 Lal .................. H10N 30/40

\* cited by examiner

DEVICE AND METHOD FOR DETECTION

BACKGROUND OF THE INVENTION

Field of the Invention

The invention relates to a detection device, and more particularly, to a detection device and a detection method.

Description of the Related Art

A conventional method of measuring a person's stress level is by analyzing HRV (Heart Rate Variability). However, since HRV analysis is usually based on 200 to 500 consecutive heartbeat signals, its delay time (e.g., about 3 to 8 minutes) makes it difficult for the user to obtain biological information in a real-time feedback report. Accordingly, there is a need to propose a novel solution for solving the problem of the prior art.

BRIEF SUMMARY OF THE INVENTION

In a preferred embodiment, the invention proposes a detection device for detecting an eyeball. The detection device includes a frame element, a transceiver, and a contact lens element. The transceiver is disposed on the frame element. The transceiver transmits a first RF (Radio Frequency) signal. The contact lens element includes a resonator. The resonator converts the first RF signal into a first ultrasonic signal. The first ultrasonic signal is transmitted to the eyeball. The resonator further converts a second ultrasonic signal from the eyeball into a second RF signal. The transceiver further receives the second RF signal.

In some embodiments, the detection device further includes a processor coupled to the transceiver. The processor estimates the current state of the eyeball by analyzing the second RF signal.

In some embodiments, the current state of the eyeball includes the pupil diameter.

In some embodiments, the frame element is an XR (Extended Reality) glasses frame.

In some embodiments, the first RF signal and the second RF signal operate in a WLAN (Wireless Local Area Network) frequency band, a Bluetooth frequency band, or an NFC (Near Field Communication) frequency band.

In some embodiments, the resonator is implemented with an FBAR (Film Bulk Acoustic Resonator).

In some embodiments, the resonator is implemented with an HBAR (High-overtone Bulk Acoustic Resonator).

In some embodiments, the resonator includes an antenna element and a piezoelectric layer. The antenna element includes a first radiation metal element and a second radiation metal element. The piezoelectric layer is disposed between the first radiation metal element and the second radiation metal element.

In some embodiments, the resonator further includes a hydrogel layer disposed adjacent to the antenna element and the piezoelectric layer.

In some embodiments, the antenna element is a dipole antenna.

In some embodiments, the thickness of the piezoelectric layer is substantially equal to 0.5 wavelength of the first ultrasonic signal or the second ultrasonic signal.

In some embodiments, the thickness of the piezoelectric layer is from 1 μm to 3 μm.

In some embodiments, the first ultrasonic signal vertically enters the eyeball, such that the eyeball generates the second ultrasonic signal.

In another preferred embodiment, the invention proposes a detection method that includes the steps of: transmitting a first RF signal via a transceiver; converting the first RF signal into a first ultrasonic signal via a resonator of a contact lens element, wherein the first ultrasonic signal is transmitted to an eyeball; converting a second ultrasonic signal from the eyeball into a second RF signal via the resonator of the contact lens element; and receiving the second RF signal via the transceiver.

In some embodiments, the detection method further includes estimating the current state of the eyeball by analyzing the second RF signal.

BRIEF DESCRIPTION OF DRAWINGS

The invention can be more fully understood by reading the subsequent detailed description and examples with references made to the accompanying drawings, wherein.

DETAILED DESCRIPTION OF THE INVENTION

Figure 1:
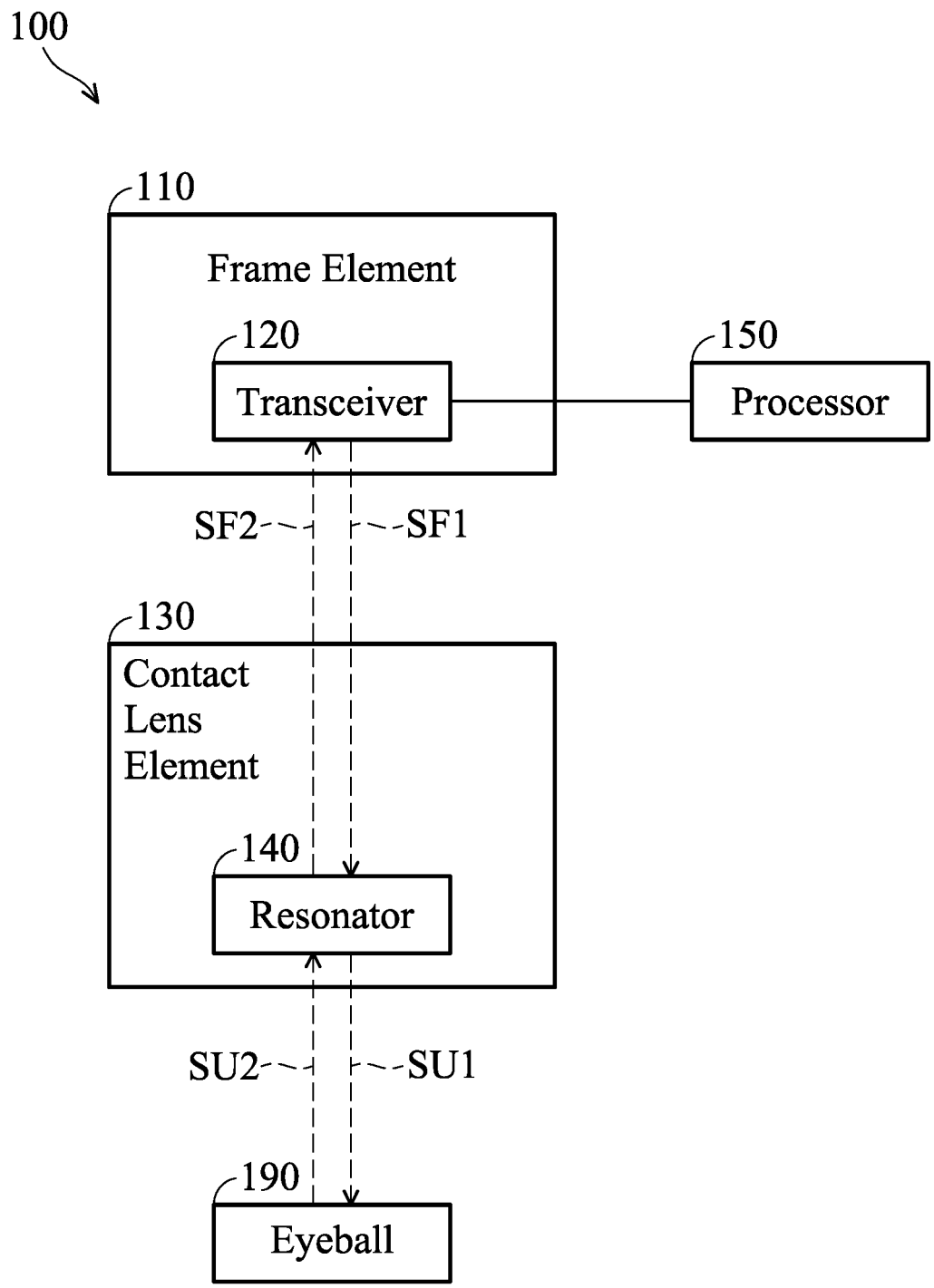
FIG. 1 is a diagram of a detection device according to an embodiment of the invention.

In order to illustrate the foregoing and other purposes, features and advantages of the invention, the embodiments and figures of the invention will be described in detail as follows.

Certain terms are used throughout the description and following claims to refer to particular components. As one skilled in the art will appreciate, manufacturers may refer to a component by different names. This document does not intend to distinguish between components that differ in name but not function. In the following description and in the claims, the terms "include" and "comprise" are used in an open-ended fashion, and thus should be interpreted to mean "include, but not limited to . . . ". The term "substantially" means the value is within an acceptable error range. One skilled in the art can solve the technical problem within a predetermined error range and achieve the proposed technical performance. Also, the term "couple" is intended to mean either an indirect or direct electrical connection. Accordingly, if one device is coupled to another device, that connection may be through a direct electrical connection, or through an indirect electrical connection via other devices and connections.

The following disclosure provides many different embodiments, or examples, for implementing different features of the subject matter provided. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

FIG. 1 is a diagram of a detection device 100 according to an embodiment of the invention. The detection device 100 may be applied to an HMD (Head Mounted Display) or a mobile device, such as an AR glasses, a smart phone, a tablet computer, or a notebook computer, but it is not limited thereto. In the embodiment of FIG. 1, the detection device 100 at least includes a frame element 110, a transceiver 120, and a contact lens element 130. It should be understood that the detection device 100 may further include other components, such as a housing, a speaker, and/or a power supply module, although they are not displayed in FIG. 1.

In some embodiments, the detection device 100 is configured to detect an eyeball 190. It should be noted that the eyeball 190 is not any portion of the detection device 100. In alternative embodiments, the detection device 100 is also configured to detect another portion of a human body.

The shape and type of the frame element 110 are not limited in the invention. In some embodiments, the frame element 110 is an XR (Extended Reality) glasses frame. For example, the aforementioned XR may include VR (Virtual Reality), MR (Mixed Reality), and/or AR (Augmented Reality).

For example, the transceiver 120 may be a radar module. The transceiver 120 is disposed on the frame element 110. The transceiver 120 can transmit a first RF (Radio Frequency) signal SF1. The contact lens element 130 includes a resonator 140. The resonator 140 can convert the first RF signal SF1 into a first ultrasonic signal SU1. The first ultrasonic signal SU1 can be further transmitted to the eyeball 190. Next, the resonator 140 can further convert a second ultrasonic signal SU2 from the eyeball 190 into a second RF signal SF2. The transceiver 120 can further receive the second RF signal SF2. In some embodiments, both the first RF signal SF1 and the second RF signal SF2 operate in a WLAN (Wireless Local Area Network) frequency band, a Bluetooth frequency band, or an NFC (Near Field Communication) frequency band, but they are not limited thereto.

Generally, the second ultrasonic signal SU2 records the relative information of the eyeball 190, and the second ultrasonic signal SU2 is further converted into the second RF signal SF2. Thus, the detection device 100 can obtain the aforementioned relative information according to the second RF signal SF2. With the design of the invention, the proposed detection device 100 can perform a real-time and dynamic detection process on the eyeball 190 of the user, so as to minimize the whole delay time.

The following embodiments will introduce different configurations and detail structural features of the detection device 100. It should be understood that these figures and descriptions are merely exemplary, rather than limitations of the invention.

In some embodiments, the detection device 100 further includes a processor 150. The processor 150 is coupled to the transceiver 120. The processor 150 can estimate the current state of the eyeball 190 by analyzing the second RF signal SF2. For example, the current state of the eyeball 190 may include the pupil diameter, but it is not limited thereto. In some embodiments, the processor 150 can determine the stress level of the user according to the current state of the eyeball 190. It should be understood that the processor 150 is merely an optional element, which is omitted in other embodiments.

Figure 2:
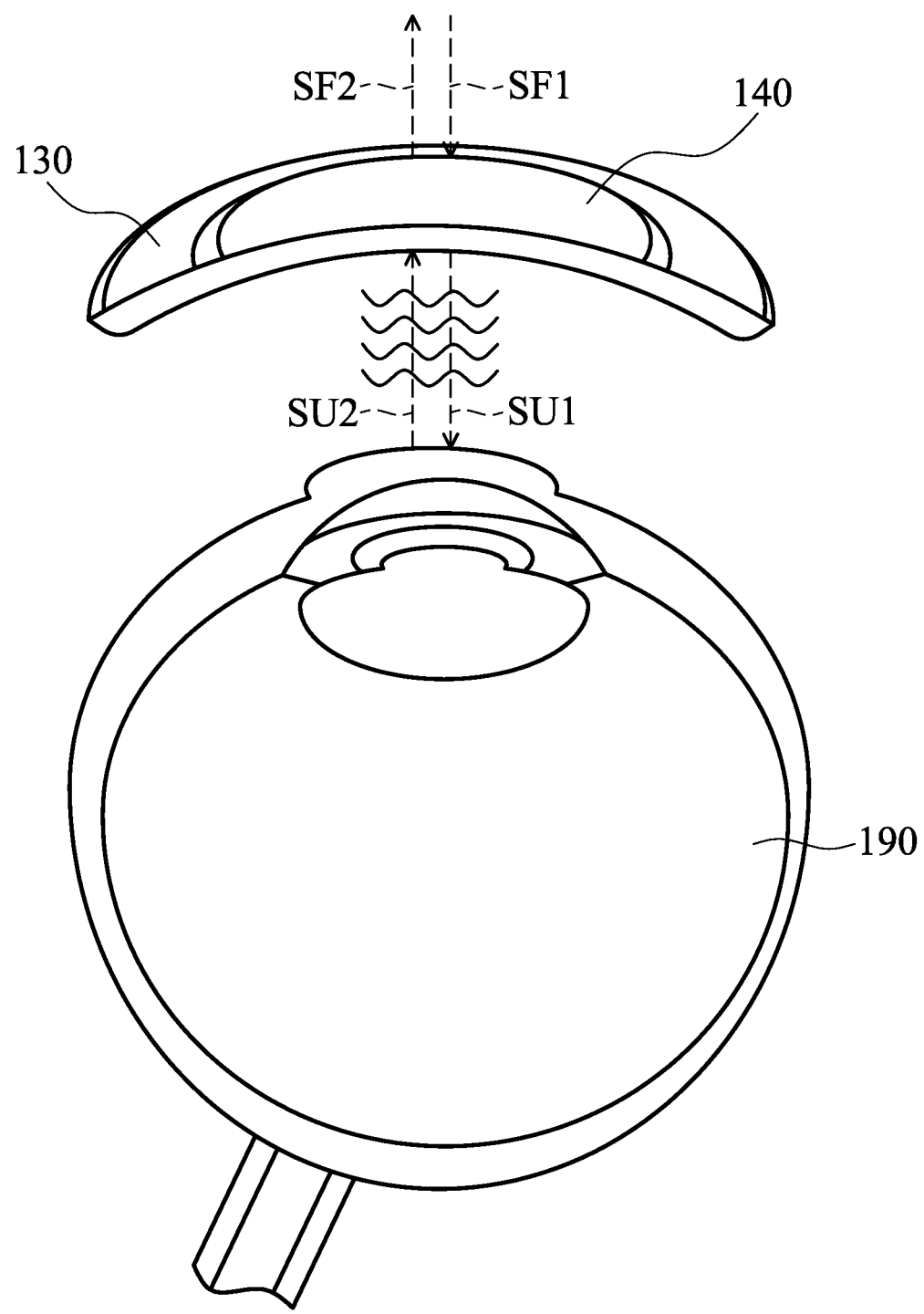
FIG. 2 is a perspective view of a contact lens element and an eyeball according to an embodiment of the invention.

FIG. 2 is a perspective view of the contact lens element 130 and the eyeball 190 according to an embodiment of the invention. In the embodiment of FIG. 2, the contact lens element 130 is disposed adjacent to the eyeball 190. It should be noted that the term "adjacent" or "close" over the disclosure means that the distance (spacing) between two corresponding elements is smaller than a predetermined distance (e.g., 10 mm or shorter), or means that the two corresponding elements directly touch each other (i.e., the aforementioned distance (spacing) between them is reduced to 0).

As mentioned above, the resonator 140 of the contact lens element 130 can convert the first RF signal SF1 into the first ultrasonic signal SU1. Next, the first ultrasonic signal SU1 can vertically enter the eyeball 190 and interact with the internal structure of the eyeball 190. In response to the first ultrasonic signal SU1, the eyeball 190 can generate the second ultrasonic signal SU2, which is considered as a reflective ultrasonic signal for recording the relative information of the eyeball 190. Next, the resonator 140 of the contact lens element 130 can further convert the second ultrasonic signal SU2 into the second RF signal SF2 for the following analysis. In some embodiments, the transmission directions of the first ultrasonic signal SU1 and the second ultrasonic signal SU2 are substantially perpendicular to a surface of the eyeball 190. That is, the first ultrasonic signal SU1 and the second ultrasonic signal SU2 are not surface waves relative to the eyeball 190.

Figure 3C:
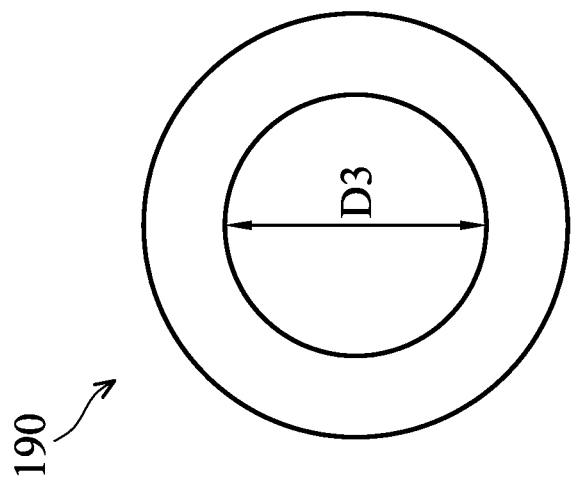
FIG. 3C is a front view of an eyeball according to an embodiment of the invention.
Figure 3B:
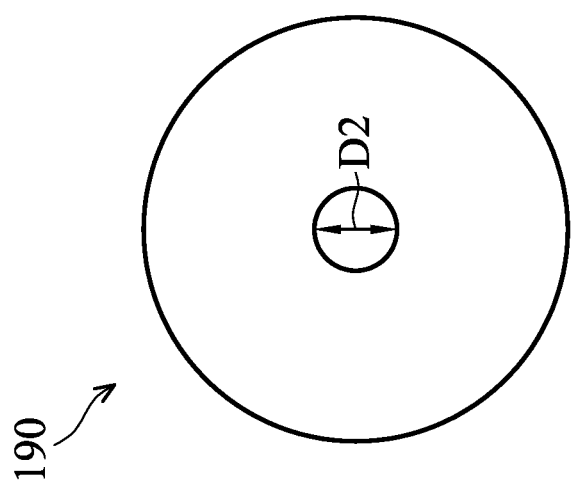
FIG. 3B is a front view of an eyeball according to an embodiment of the invention.
Figure 3A:
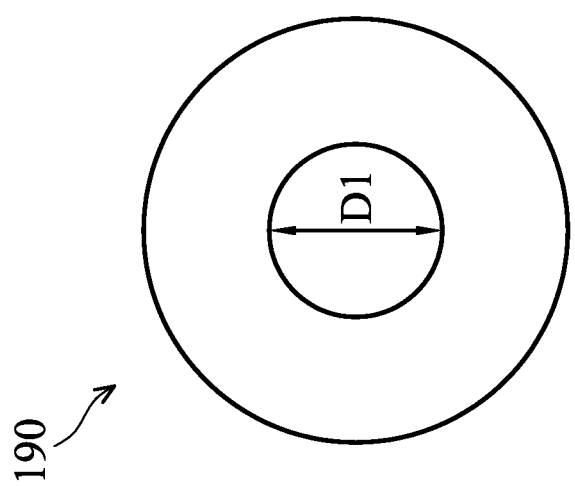
FIG. 3A is a front view of an eyeball according to an embodiment of the invention.

FIG. 3A is a front view of the eyeball 190 according to an embodiment of the invention. In the embodiment of FIG. 3A, the eyeball 190 corresponds to a relatively median pupil diameter D1. FIG. 3B is a front view of the eyeball 190 according to an embodiment of the invention. In the embodiment of FIG. 3B, the eyeball 190 corresponds to a relatively small pupil diameter D2. FIG. 3C is a front view of the eyeball 190 according to an embodiment of the invention. In the embodiment of FIG. 3C, the eyeball 190 corresponds to a relatively large pupil diameter D3. Thus, the detection device 100 can understand the current state of the eyeball 190 by analyzing the second ultrasonic signal SU2. For example, the pupil diameter of the eyeball 190 may be similar to any one of FIG. 3A, FIG. 3B and FIG. 3C. In this way, a feedback report of biological information can be obtained by counting the time series of pupil diameter changes.

In some embodiments, the resonator 140 of the contact lens element 130 is implemented with an FBAR (Film Bulk Acoustic Resonator). However, the invention is not limited thereto. In alternative embodiments, the resonator 140 of the contact lens element 130 is implemented with an HBAR (High-overtone Bulk Acoustic Resonator). In addition, the resonator 140 of the contact lens element 130 may include a thin-film piezoelectric substrate which is biocompatible, such as ZnO (Zinc Oxide), AlN (Aluminum Nitride), etc. (not shown).

Figure 4:
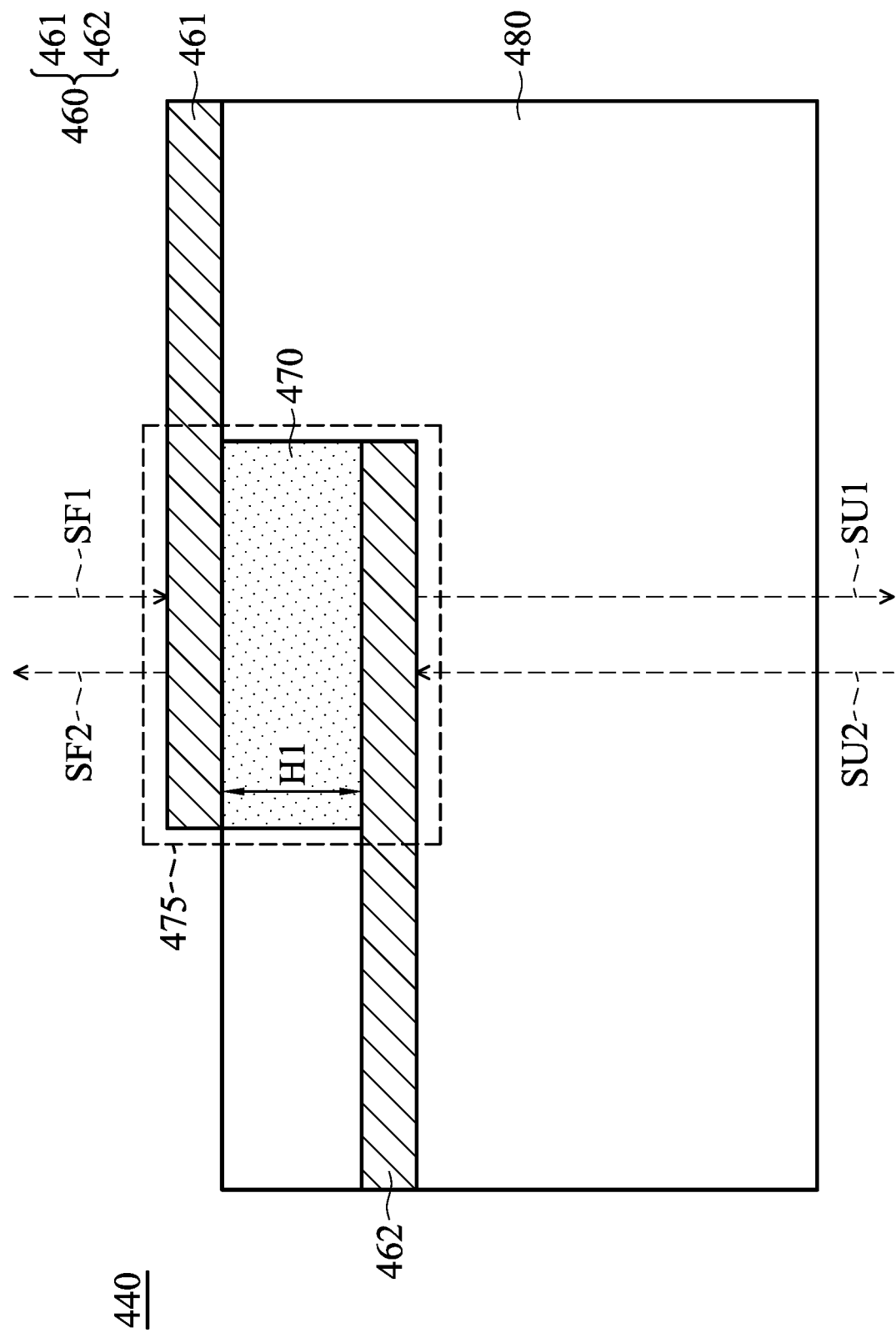
FIG. 4 is a sectional view of a resonator according to an embodiment of the invention.

FIG. 4 is a sectional view of a resonator 440 according to an embodiment of the invention. The resonator 440 is applicable to the aforementioned detection device 100. In the embodiment of FIG. 4, the resonator 440 is implemented with a multilayer dielectric substrate, and it at least includes an antenna element 460 and a piezoelectric layer 470. Specifically, the antenna element 460 includes a first radiation metal element 461 and a second radiation metal element 462, and the piezoelectric layer 470 is disposed between the first radiation metal element 461 and the second radiation metal element 462. For example, if the antenna element 460 is a dipole antenna, the first radiation metal element 461 may be a positive radiator of the dipole antenna, and the second radiation metal element 462 may be a negative radiator of the dipole antenna, but they are not limited thereto.

A sandwich structure 475 is formed by the antenna element 460 and the piezoelectric layer 470, and it is used for conversion between RF signals and ultrasonic signals. In order to meet the resonant condition of the sandwich structure 475, the thickness H1 of the piezoelectric layer 470 can be substantially equal to 0.5 wavelength (212) of the first ultrasonic signal SU1 or the second ultrasonic signal SU2. For example, the thickness H1 of the piezoelectric layer 470 may be from 1 μm to 3 μm, but it is not limited thereto. The thickness H1 of the piezoelectric layer 470 may be mainly relative to the piezoelectric material properties and the operational frequency. In some embodiments, the resonator 440 further includes a hydrogel layer 480, which is disposed adjacent to the antenna element 460 and the piezoelectric layer 470. The hydrogel layer 480 is considered as a transparent portion of the contact lens element 130.

It should be understood that the shape and type of the antenna element 460 are not limited in the invention. In alternative embodiments, the antenna element 460 may be modified to a monopole antenna, a loop antenna, a helical antenna, a patch antenna, a PIFA (Planar Inverted F Antenna), or a chip antenna.

Figure 5:
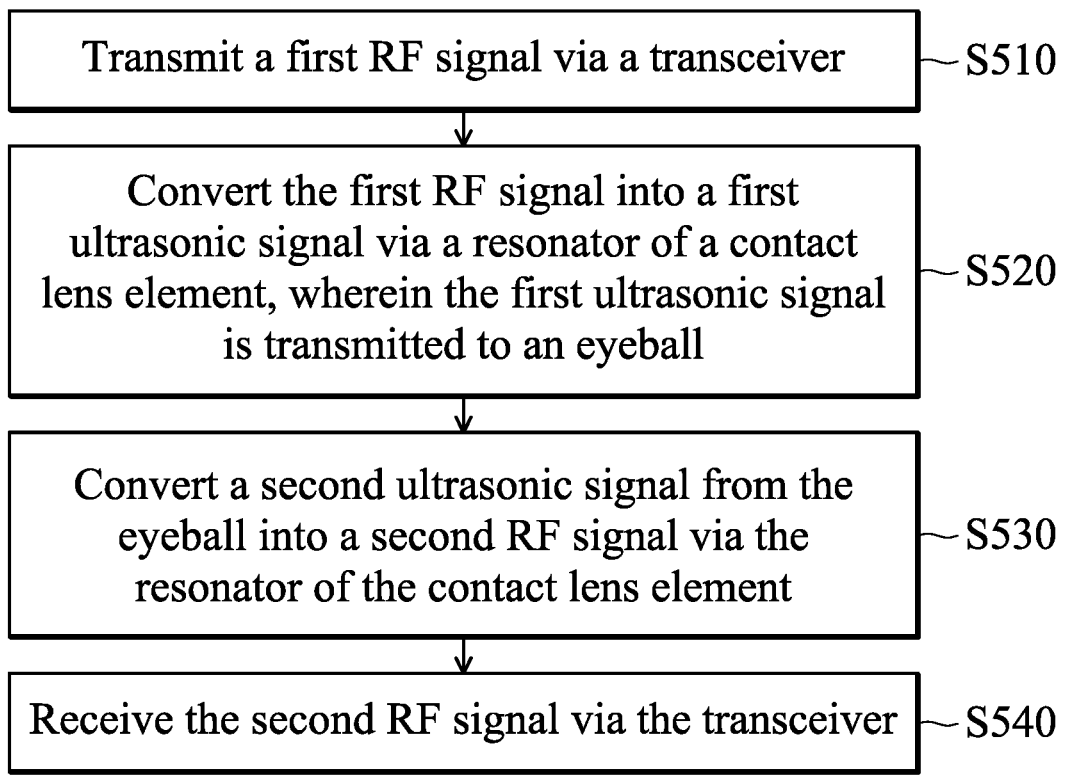
FIG. 5 is a flowchart of a detection device according to an embodiment of the invention.

FIG. 5 is a flowchart of a detection device 500 according to an embodiment of the invention. To begin, in step S510, a first RF signal is transmitted by a transceiver. In step S520, the first RF signal is converted into a first ultrasonic signal by a resonator of a contact lens element. The first ultrasonic signal is further transmitted to an eyeball. In step S530, a second ultrasonic signal from the eyeball is converted into a second RF signal by the resonator of the contact lens element. Finally, in step S540, the second RF signal is received by the transceiver. It should be understood that these steps are not required to be performed in order, and every feature of the embodiments of FIGS. 1 to 4 may be applied to the detection method of FIG. 5.

The invention proposed a novel detection device and a novel detection method. In comparison to the conventional design, the invention has at least the advantages of quickly obtaining the biological information, minimizing the whole device size, and reducing the whole manufacturing cost. Therefore, the invention is suitable for application in a variety of devices.

Note that the above element parameters are not limitations of the invention. A designer can fine-tune these setting values according to different requirements. It should be understood that the detection device and detection method of the invention are not limited to the configurations of FIGS. 1-5. The invention may include any one or more features of any one or more embodiments of FIGS. 1-5. In other words, not all of the features displayed in the figures should be implemented in the detection device and detection method of the invention.

The method of the invention, or certain aspects or portions thereof, may take the form of program code (i.e., executable instructions) embodied in tangible media, such as floppy diskettes, CD-ROMS, hard drives, or any other machine-readable storage medium, wherein, when the program code is loaded into and executed by a machine such as a computer, the machine thereby becomes an apparatus for practicing the methods. The methods may also be embodied in the form of program code transmitted over some transmission medium, such as electrical wiring or cabling, through fiber optics, or via any other form of transmission, wherein, when the program code is received and loaded into and executed by a machine such as a computer, the machine becomes an apparatus for practicing the disclosed methods. When implemented on a general-purpose processor, the program code combines with the processor to provide a unique apparatus that operates analogously to application-specific logic circuits.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

It will be apparent to those skilled in the art that various modifications and variations can be made in the invention. It is intended that the standard and examples be considered as exemplary only, with a true scope of the disclosed embodiments being indicated by the following claims and their equivalents.

What is claimed is:

1. A detection device for detecting an eyeball, and comprising:
   a frame element;
   a transceiver, disposed on the frame element, and transmitting a first RF (Radio Frequency) signal; and
   a contact lens element, comprising a resonator, wherein the resonator converts the first RF signal into a first ultrasonic signal, and the first ultrasonic signal is transmitted to the eyeball;
   wherein the resonator further converts a second ultrasonic signal from the eyeball into a second RF signal, and the transceiver further receives the second RF signal,
   wherein the resonator comprises:
   an antenna element, comprising a first radiation metal element and a second radiation metal element; and
   a piezoelectric layer, disposed between the first radiation metal element and the second radiation metal element.

2. The detection device as claimed in claim 1, further comprising:
   a processor, coupled to the transceiver, wherein the processor estimates a current state of the eyeball by analyzing the second RF signal.

3. The detection device as claimed in claim 2, wherein the current state of the eyeball comprises a pupil diameter.

4. The detection device as claimed in claim 1, wherein the frame element is an XR (Extended Reality) glasses frame.

5. The detection device as claimed in claim 1, wherein the first RF signal and the second RF signal operate in a WLAN (Wireless Local Area Network) frequency band, a Bluetooth frequency band, or an NFC (Near Field Communication) frequency band.

6. The detection device as claimed in claim 1, wherein the resonator is implemented with an FBAR (Film Bulk Acoustic Resonator).

7. The detection device as claimed in claim 1, wherein the resonator is implemented with an HBAR (High-overtone Bulk Acoustic Resonator).

8. The detection device as claimed in claim 1, wherein the first ultrasonic signal vertically enters the eyeball, such that the eyeball generates the second ultrasonic signal.

9. The detection device as claimed in claim 1, wherein the resonator further comprises:
   a hydrogel layer, disposed adjacent to the antenna element and the piezoelectric layer.

10. The detection device as claimed in claim 1, wherein the antenna element is a dipole antenna.

11. The detection device as claimed in claim 1, wherein a thickness of the piezoelectric layer is substantially equal to 0.5 wavelength of the first ultrasonic signal or the second ultrasonic signal.

12. The detection device as claimed in claim 1, wherein a thickness of the piezoelectric layer is from 1 μm to 3 μm.

13. A detection method, comprising the steps of:
   transmitting a first RF signal via a transceiver;
   converting the first RF signal into a first ultrasonic signal via a resonator of a contact lens element, wherein the first ultrasonic signal is transmitted to an eyeball;
   converting a second ultrasonic signal from the eyeball into a second RF signal via the resonator of the contact lens element; and
   receiving the second RF signal via the transceiver,
   wherein the resonator comprises an antenna element and a piezoelectric layer, the antenna element comprises a first radiation metal element and a second radiation metal element, and the piezoelectric layer is disposed between the first radiation metal element and the second radiation metal element.

14. The detection method as claimed in claim 13, wherein the first ultrasonic signal vertically enters the eyeball, such that the eyeball generates the second ultrasonic signal.

15. The detection method as claimed in claim 13, further comprising:
   estimating a current state of the eyeball by analyzing the second RF signal.

16. The detection method as claimed in claim 15, wherein the current state of the eyeball comprises a pupil diameter.

17. The detection method as claimed in claim 13, wherein the first RF signal and the second RF signal operate in a WLAN frequency band, a Bluetooth frequency band, or an NFC frequency band.

18. The detection method as claimed in claim 13, wherein the resonator is implemented with an FBAR.

19. The detection method as claimed in claim 13, wherein the resonator is implemented with an HBAR.

* * * * *